United States Patent [19]
Phillips

[11] Patent Number: 5,425,782
[45] Date of Patent: Jun. 20, 1995

[54] ALIGNMENT FIXTURE FOR PROSTHETIC DEVICE

[76] Inventor: Van L. Phillips, P.O. Box 1873, Rancho Santa Fe, Calif. 92067

[21] Appl. No.: 183,631

[22] Filed: Jan. 18, 1994

Related U.S. Application Data

[63] Continuation of Ser. No. 849,523, Mar. 11, 1992, abandoned.

[51] Int. Cl.⁶ .............................................. A61F 2/62
[52] U.S. Cl. ...................................... 623/38; 403/87; 403/90
[58] Field of Search ...................... 623/38, 27; 403/84, 403/87, 90

[56] References Cited

U.S. PATENT DOCUMENTS

| | | |
|---|---|---|
| 3,206,235 | 9/1965 | Albinson et al. . |
| 3,414,908 | 12/1968 | Waggott et al. . |
| 3,422,462 | 1/1969 | Finnieston ............................. 623/38 |
| 3,538,516 | 11/1970 | Bailey et al. . |
| 3,659,294 | 5/1972 | Glabiszewski . |
| 3,671,978 | 6/1972 | May . |
| 3,958,904 | 5/1976 | Rusbach ............................... 403/90 |
| 3,982,278 | 9/1976 | May . |
| 4,007,496 | 2/1977 | Glabiszewski . |
| 4,074,542 | 2/1978 | Hankosky et al. . |
| 4,089,072 | 5/1978 | Glabiszewski . |
| 4,161,042 | 7/1979 | Cottingham . |
| 4,186,449 | 2/1980 | Horvath . |
| 4,216,550 | 8/1980 | Thompson . |
| 4,302,856 | 12/1981 | May . |
| 4,395,783 | 8/1983 | Eyre et al. . |
| 4,475,314 | 10/1984 | Faix et al. .......................... 403/90 X |
| 4,536,898 | 8/1985 | Palfray . |

(List continued on next page.)

FOREIGN PATENT DOCUMENTS

| | | | |
|---|---|---|---|
| 0267347 | 5/1988 | European Pat. Off. ............... | 623/38 |
| 1502061 | 11/1967 | France .................................. | 623/38 |

(List continued on next page.)

OTHER PUBLICATIONS

"The Seattle Prosthesis Foot—A Design for Active Sports: Preliminary Studies," E. M. Burgess, M.D., et al., *Orthotics and Prosthetics Journal*, vol. 37, No. 1, Spring 1983.

The Seattle Foot—Winner of Presidential Design Aware—Jan. 30, 1985.

Copes/Bionic Ankle.

*L.A. Times* View Section, "Seattle Foot," Jun. 12, 1984.

Campbell Childs, Jr. Product Catalog.

(List continued on next page.)

*Primary Examiner*—David H. Willse
*Attorney, Agent, or Firm*—Knobbe, Martens, Olson & Bear

[57] ABSTRACT

A fixture permitting adjustment of the position and axial alignment of a prosthesis is characterized by a first attachment member associated with a socket attached to the wearer's stump, and by the fixture's ability to be adjusted without the necessity of removing the socket from the wearer's stump. A second attachment member is operatively attached to the prosthesis, and adjustable attachment means operatively connects the second attachment member to the first attachment member. The adjustable attachment means includes a central bolt member which may be accessed for adjustment without removing the socket from the wearer. The bolt member preferably extends through a rectilinear central opening in the first attachment member, providing a range of selectable lateral positions of the second attachment member with respect to the first attachment member. The adjustable attachment means also preferably includes a frustoconical member disposed between the first and second attachment members, and auxiliary adjustment members operatively engaged between the second attachment member and the frustoconical member to permit the axial alignment of the second attachment member to be adjusted with respect to the first attachment member.

18 Claims, 2 Drawing Sheets

U.S. PATENT DOCUMENTS

| | | | |
|---|---|---|---|
| 4,608,054 | 8/1986 | Schröder | 623/39 |
| 4,659,053 | 4/1987 | Holley et al. | 403/90 X |
| 4,676,800 | 6/1987 | Chen . | |
| 4,728,336 | 3/1988 | Cooper . | |
| 4,883,494 | 11/1989 | Cooper . | |
| 4,969,911 | 11/1990 | Greene . | |
| 5,013,325 | 5/1991 | Rennerfelt | 623/38 |
| 5,019,109 | 5/1991 | Voisin . | |
| 5,047,063 | 9/1991 | Chen | 623/38 |

FOREIGN PATENT DOCUMENTS

| | | | |
|---|---|---|---|
| 2410998 | 8/1979 | France | 623/38 |
| 2630641 | 11/1989 | France | 606/88 |
| 454046 | 3/1988 | Sweden . | |
| 446373 | 9/1996 | Sweden . | |
| 1371996 | 10/1974 | United Kingdom . | |
| 2089216 | 6/1982 | United Kingdom . | |
| 0721094 | 3/1980 | U.S.S.R. | 623/38 |
| 1026803 | 7/1983 | U.S.S.R. | 623/38 |
| 1217404 | 3/1986 | U.S.S.R. | 623/38 |
| 1553115 | 3/1990 | U.S.S.R. | 623/38 |

OTHER PUBLICATIONS

"The Flex-Shin: A Composite Material for Use in Flexible Shank Below-Knee Prosthesis," Thurston, et al., *Prosthetics and Orthotics International.*
Otto Bock Lower Extremity Modular Prostheses (4 pages).
Centri Built-in One-point Alignment (3 pages).
Hosmer Intermed (4 pages).
USMC Modular Titanium Components (2 pages).

ALIGNMENT FIXTURE FOR PROSTHETIC DEVICE

This application is a continuation of application Ser. No. 07/849,523, filed 11, Mar. 1992, now abandoned.

BACKGROUND OF THE INVENTION

This invention relates to prostheses in general, and specifically to a fixture assembly by which a prosthetic device may be laterally positioned and axially aligned with respect to a wearer, in any of a range of positions and alignments. The invention provides a range and ease of adjustability not present in the prior art.

Prostheses are typically attached to a wearer by the use of a socket on the wearer's stump. It is known to utilize a socket adaptor to permit the prosthesis to be pivoted to a desirable angle with respect to the socket, and/or to provide some range of lateral (in all horizontal directions) position adjustability as between the socket and the prosthesis. Both of these adjustments permit greater tolerances in the fabrication and mounting of a socket on a wearer.

Prior art socket adaptors have numerous shortcomings. For example, many cannot be adjusted without removing the socket from the wearer. Because sockets normally fit snugly on the wearer's stump, removal of the socket can be a time-consuming process, and can sometimes cause discomfort to the wearer. Moreover, in order to accurately and appropriately adjust the alignment and position of the prosthesis, the socket may have to be removed repeatedly.

Accordingly, a substantial amount of time and energy is involved in adjusting and aligning a prosthesis using known socket adaptors.

Additionally, prior art adaptors permit the prosthesis to be selectably shifted or positioned laterally with respect to the socket. Where bolt and nut assemblies are used to assemble the components of these adaptors, this lateral positioning is sometimes achieved by providing an oversized opening about the bolt. Within the confines of that opening, the prosthesis may be moved laterally prior to tightening the bolt, effectively allowing the wearer and/or the prosthetist to position the prosthesis at a selected location.

The range of lateral positioning provided by prior art devices is substantially limited, however, because of the typical circular shape of the oversized openings. Such a circular shape does not permit the prosthesis to be offset or shifted to its maximum forward/backward position simultaneously with its maximum side-to-side position. Accordingly, prior art adaptors must be carefully affixed to the socket, to ensure that the opening will accommodate the desired lateral positioning of the prosthesis with respect thereto.

OBJECTS AND ADVANTAGES OF THE INVENTION

It is, therefore, an object of my invention to provide an alignment fixture assembly for prosthetic devices which is characterized by an ease of adjustability not found in the prior art. Specifically, the invention permits the angular alignment and lateral position (anterior/posterior and medial/lateral) of the prosthesis to be adjusted relative to the socket, without the necessity of removing the socket from the wearer's stump.

In a preferred embodiment, as described below, the improved socket adaptor includes a first attachment member operatively associated with or incorporated in the socket. A second attachment member is adjacent the first attachment member and is adapted for operative attachment to the prosthesis. Adjustable attachment means operatively attaches the second attachment member to the first attachment member.

In order that the aforementioned position and alignment adjustment may be accomplished without removing the socket means from the wearer's stump, the adjustable attachment means of the preferred embodiment includes a central bolt and nut assembly. A central bolt member is disposed through openings in the first and second attachment members, and the bolt and nut assembly may be tightened and loosened without removing the socket from the wearer. When the central bolt and nut assembly (and any auxiliary adjustment means, as described below) is loosened, the fixture may be positioned and aligned as desired, with relative ease.

Because any repeated adjustments can be made without removing the socket from the wearer, the invention provides substantial savings in time and energy necessary to properly adjust the prosthesis, as well as substantially reducing the discomfort and inconvenience to the wearer.

It is a further object of my invention to provide a fixture of the aforementioned character which permits a broader selection of lateral positions for the prosthesis with respect to the socket. As indicated above, prior art adaptors typically utilize circular openings in the first attachment member. When that circular opening is larger than the central bolt, the central bolt may be positioned laterally within the circular opening, correspondingly permitting the prosthesis to be selectively positioned prior to tightening the bolt.

The preferred embodiment of my instant invention provides a non-circular (for example, rectilinear) opening in the first attachment member. The non-circularity permits the central bolt member (and correspondingly, the prosthesis) to be laterally shifted into positions not achievable with prior art devices. This reduces the degree of precision necessary for the placement of the first attachment member on the socket, and/or permits the prosthetist and wearer to adjust the prosthesis into positions not otherwise accessible.

It is yet another object of my invention to provide an adjustable fixture assembly of the above-referenced character in which the first attachment member has a central longitudinal axis and the second attachment member has a central longitudinal axis, and the adjustable attachment means includes a frustoconical member disposed between the first attachment member and the second attachment member, whereby the alignment of the axis of the second attachment member with respect to the axis of the first attachment member may be selected from a range of alignments and retained in the selected alignment by the adjustable attachment means.

In the preferred embodiment, the assembly includes auxiliary adjustment means between the second attachment member and the frustoconical member. The auxiliary adjustment means preferably includes a plurality of adjustment screws threadedly engaged through the periphery of the second attachment member and in confronting contact with the frustoconical member. A protective shield means is also preferably disposed between the frustoconical member and the plurality of adjustment screws to protect the frustoconical member from deterioration.

Other objects and advantages of the invention will be apparent from the following specification and the accompanying drawings, which are for the purpose of illustration only.

DESCRIPTION OF PREFERRED EMBODIMENT

Figures 1, 2, 3, 4:
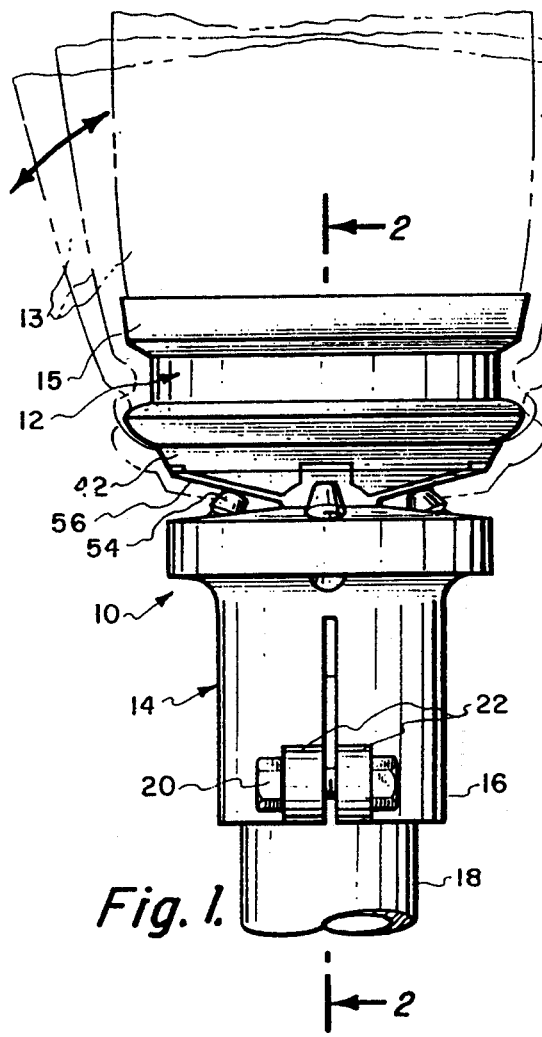
FIG. 1 is an elevation view of an adjustable fixture assembly constructed in accordance with the teachings of the invention.
FIG. 2 is a side elevation sectional view, taken along line 2—2 of FIG. 1.
FIG. 3 is a plan view, taken along line 3—3 of FIG. 2.
FIG. 4 is a partially sectional bottom view, taken along line 4—4 of FIG. 2.

Referring to the drawings, and particularly to FIG. 1 thereof, I show a preferred embodiment of an adjustable fixture assembly 10 constructed in accordance with the teachings of the invention and including a first attachment member 12 operatively attached to or incorporated in a prosthetic socket (shown in phantom as socket 13). For example, the socket may be molded or formed about an annular lip 15 on the first attachment member.

The socket may be any of a wide variety of prosthetic sockets useful for operatively attaching a prosthetic device to the stump of an amputee. Although the drawings and description herein illustrate a lower leg prosthetic socket, the invention may be readily utilized for arm, upper leg or other prosthetic needs.

The first attachment member 12 is preferably cast or fabricated from a suitably strong, lightweight material such as fiberglass, carbon, graphite, titanium, aluminum, steel, a composite of some or all of these materials, or the like. Similar materials and techniques may be used to fabricate a second attachment member 14, adjacent the first attachment member 12 in the fixture assembly 10.

The second attachment member 14 is adapted to be operatively attached to a prosthesis, such as a prosthetic foot. In the embodiments shown in the drawings herewith, the attachment member 14 having a split-sleeve portion 16 that slidably receives a known prosthetic pylon tube 18 (to which a prosthetic foot, not shown, could be attached). The split-sleeve portion 16 preferably includes a nut and bolt assembly 20 operably disposed through projections 22, whereby the nut and bolt assembly 20 may be tightened to hold the pylon in the split-sleeve portion 16 or loosened to permit its removal or repositioning therein.

The preferred embodiment further includes attachment means 30, FIG. 2, operatively attaching the second attachment member 14 to the first attachment member 12. In the preferred embodiment, the attachment means 30 includes a central nut and bolt assembly 32, 34.

The central bolt member 32 is preferably disposed through a centrally-located opening 36 in the first attachment member 12, and through a centrally-located opening 38 in the second attachment member 14.

In order to permit the second attachment member 14 (and correspondingly the pylon 18 and the prosthesis, not shown) to be desirably shifted or positioned laterally with respect to the first attachment member 12, the opening 36 is larger than the bolt member 32. As best shown in FIG. 3, the opening 36 is non-circular in plan view. For purposes of example, the opening 36 is illustrated in a rectilinear shape, although those skilled in the art will understand that any of a range of non-circular shapes may be utilized with efficacy (and circular shapes may even be utilized, although without the benefits of non-circularity discussed herein).

An eye-shaped washer 40 is preferably provided to prevent the nut 34 from falling or pulling through the opening 36. Although circular washers (or oval or other shapes) could be utilized with efficacy in various embodiments of my invention, the eye shape is preferable because it provides both good load transfer and good lateral adjustability. Regarding load transfer, the "points" of the eye permit the forces on the nut 34 to be transferred across a longer lever arm than would a shorter radius of washer, thereby providing better leverage and load transfer.

With respect to the lateral adjustability provided by the eye shape, the flat sides of the shape permit the bolt assembly to be laterally positioned anywhere within the opening 36. The preferred symmetry of the shape of the washer 40 permits the lateral adjustment to occur multidirectionally; that is, the washer 40 does not have to be oriented any particular direction in order for the bolt 32 to be laterally positioned within the opening 36.

As indicated above, the washer 40 is sized to permit it to move with the bolt and nut assembly 32, 34 during the selection of a lateral position for the second attachment member 14 with respect to the first attachment member 12. The non-circular shape of the opening 36 permits the bolt member, when in a loosened state, to be shifted or slid into positions (for example, the corners of the rectangle 36, FIG. 3) in which it could not be placed if the opening 36 were circular or oval.

As those skilled in the art will understand, the first and second attachment members 12 and 14 have respective longitudinal axes that are both approximately parallel to the bolt member 32 as it is illustrated in FIG. 2. Because the fabrication and fitting of the socket 13 does not readily lend itself to precision orientation of the attachment member 12 thereon or therein, it is useful and desirable to provide an adjustment mechanism whereby the axis of the second attachment member 14 may be secured in other than the "straight-up-and-down" alignment of FIG. 2.

By providing such an adjustability, the precision with which the first attachment member 12 must be attached to the socket 13 is reduced substantially. Examples of the respective longitudinal axes in misalignment are illustrated in phantom in FIG. 1.

In order to permit this axial alignment and adjustment to be readily achieved, the preferred attachment means 30 further includes a frustoconical member 42 disposed between the first attachment member 12 and the second attachment member 14, whereby the alignment of the axis of the second attachment member with respect to the axis of the first attachment member may be selected from a range of alignments and retained in the selected alignment by the adjustable attachment means 30.

To achieve the pivotal adjustability between the first and second attachment members 12 and 14, a spherical central hub 44 is preferably provided on the frustoconical member 42. A matingly shaped cavity or depression 46 is provided in the second attachment member 14. A tapering hole 47 is provided through the frustoconical member 42 to permit the bolt member 32 to be "tilted" into the desired axial alignment, if necessary, as more fully described below. The hole 38 in the second attachment member 14 is similarly tapered for the same reason.

Pivotally mating interfaces are also provided at other locations in the fixture. One such interface is between the head 33 of the central bolt 32 and the second attachment member 14. As illustrated in FIG. 2, a spherical hub section 48 is disposed about the central hole 38, and is in confronting contact with a washer 50 adjacent the bolt head 33. At the other end of the central nut and bolt assembly 32, 34, a spherical washer 35 underlies the nut 34 in slidingly mating contact with a spherical depression 41 in the washer 40.

These pivotally mating interfaces permit the ready selection and/or adjustment of the angular alignment of the axis of the second attachment member 14 with respect to the first attachment member 12. After a particular axial alignment is selected, the bolt and nut assembly 32, 34 may be tightened to frictionally hold the assembly in the desired alignment.

The adjustable attachment means 30 further preferably includes auxiliary adjustment means 52 between the second attachment member and the frustoconical member. In the preferred embodiment, the auxiliary adjustment means includes a plurality of adjustment screws 54 threadedly engaged through the periphery of the second attachment member and in confronting contact with the frustoconical member 42. This threaded engagement is preferably accomplished by molding threaded inserts 55 into member 42 during its fabrication.

As more thoroughly described below, the adjustment screws 54 provide an enhanced level of fine-tuning and ease of adjustability of the axial alignment of the prosthesis with respect to the socket 13.

The auxiliary adjustment means 52 further includes protective shield means 56, FIGS. 2 and 4, disposed between the frustoconical member and the plurality of adjustment screws 54. The shield means 56 is positioned to protect the frustoconical member 42 from deterioration such as gouging caused, for example, by the pressure and friction exerted by the screws 54. The shield 56 preferably includes a central ring 57 and tang portions 59 on which the screws 54 impinge. The shield means 56 may be bonded onto the frustoconical member 42 to prevent rotation of the prosthesis about the central longitudinal axis of the bolt member 32.

Figure 5:
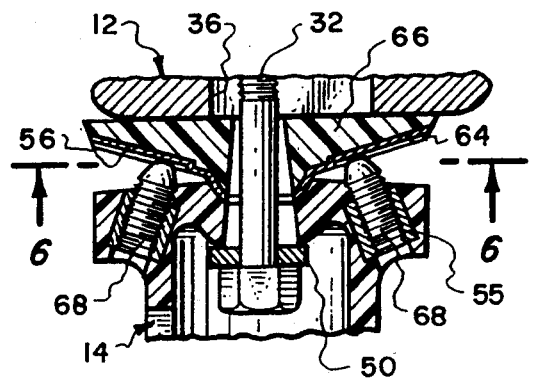
FIG. 5 is a cutaway sectional elevation view of an alternative embodiment of the invention.
Figure 6:
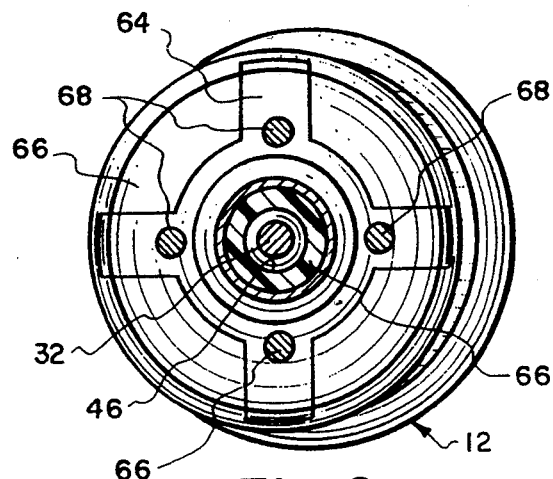
FIG. 6 is a sectional view, taken along line 6—6 of FIG. 5.
Figure 7:
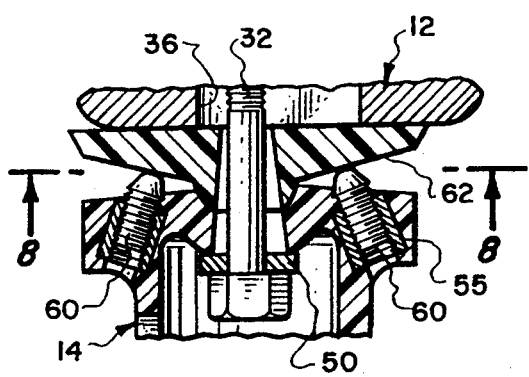
FIG. 7 is a cutaway sectional elevation view of another alternative embodiment of the invention.
Figure 8:
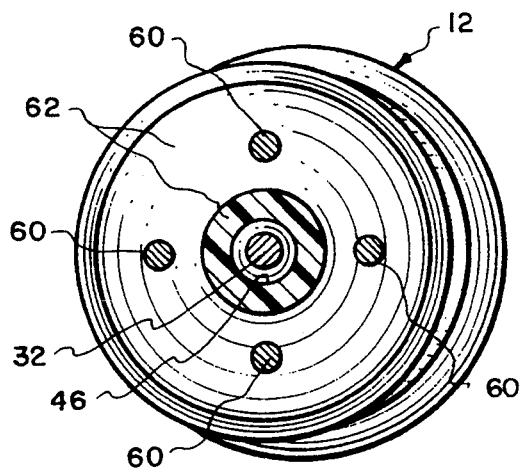
FIG. 8 is a sectional view, taken along line 8—8 of FIG. 7.

The alternative embodiments illustrated in FIGS. 5–8 are identical in structure and function to that of the preferred embodiment, with the exception of the contact between the adjustment screws 54 and the frustoconical member 42. In the embodiment of FIGS. 7 and 8, for example, no protective shield 56 is provided. Instead, adjustment screws 60 directly contact the frustoconical member 62. In the embodiment of FIGS. 5 and 6, depressions 64 on the frustoconical member 66 are oriented to receive the ends of the adjustment screws 68. These depressions 64 help prevent undesirable rotation of the prosthesis about the longitudinal central axis of the second attachment member, such as might occur under extreme twisting forces or if the frictional forces of the fixture assembly 10 were not adequate.

Figure 9:
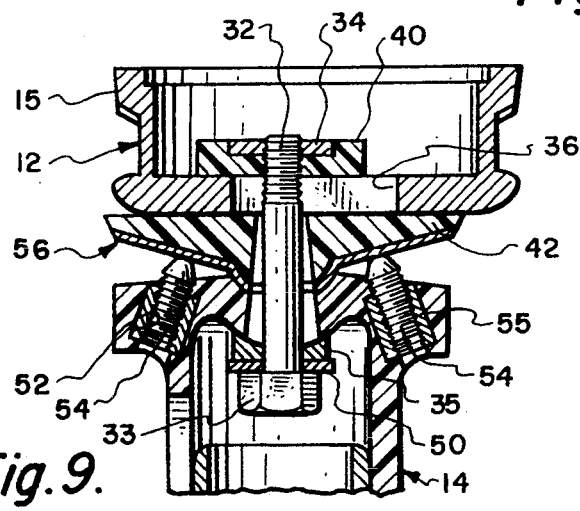
FIG. 9 is a side elevation sectional view, similar to the view of FIG. 2, illustrating an alternative embodiment of the central nut and bolt assembly.

In the embodiment of FIG. 9, the washer 40 is shown with a nut 34 set therein. The nut is preferably molded into the washer 40 at the time of its fabrication, but any of a variety of methods can be utilized to affix the nut to the washer. By recessing the nut 34 into the washer 40, the height (and corresponding weight) of the first attachment member 12 can be reduced. As those skilled in the art will understand, reduction of the weight of the prostheses is important.

In order to provide the desired axial alignment adjustability, a spherical washer 35 underlies washer 50 adjacent the bolt head 33 and confronts the spherical hub section 48 in frictionally-gripping engagement (when the bolt assembly is tightened). In this embodiment, the bolt 32 remains axially aligned parallel to the longitudinal axis of the first attachment member 12. Any adjustment of the axial alignment of the fixture assembly 10 occurs by pivoting the second attachment member 14 with respect to both the bolt 32 and the first attachment member 12.

Except where otherwise described above or where otherwise obvious to those skilled in the art, the various components of the fixture assembly 10 are preferably fabricated or molded by known processes from fiberglass, resin, graphite, titanium, aluminum, steel, composite, or other suitably strong, lightweight material. Examples of such exceptions would include the central bolt and nut assembly 32, 34 and the adjustment screws 54, both of which are preferably manufactured from a lightweight, strong metal.

A preferred method of utilizing the assembly of the invention is now described, by which the aforementioned ease of adjustability will become apparent. As those skilled in the art will understand, this method may be utilized both before and after placing the socket on the wearer.

In addition, whenever the method requires loosening or tightening of the central nut and bolt assembly 32, 34, those skilled in the art will understand that the pylon 18 should be removed to provide convenient access to the bolt head 33 (through the use of a ratchet extension or the like). Further regarding the loosening and tightening of the central nut and bolt assembly 32, 34, those skilled in the art will understand that all necessary loosening and tightening can occur without access to the nut 34, simply by accessing the bolt head 33.

First, the auxiliary screws 54 are unscrewed, so as to move out of contact with the frustoconical member 42. The central bolt and nut assembly 32, 34 is then tightened to the desired final tension, and then backed-off (loosened) one turn. This slight loosening of the main bolt and nut assembly 32, 34 permits the assembly to be shifted for purposes both of lateral positioning of the bolt member 32 within the opening 36 and of axial alignment of the second attachment member 14 with respect to the first attachment member 12.

After the desired lateral position and axial alignment has been selected, the auxiliary screws 54 are then tightened to the desired final tension. Normally, the screws 54 will extend equally from the second attachment member 14, to permit the lateral position of the fixture to be selected while there is no "tilt" to the fixture. The angular alignment can be adjusted subsequently, as described below.

Although this arrangement (the auxiliary screws extended) frictionally locks the assembly in the desired orientation and position, there may be a gap between the hub section 44 and its correspondingly mating surface 46 on the second attachment member 14. In order to maximize the life and strength of the tightened fixture, it is desirable to eliminate that gap and bring surfaces 44 and 46 into frictional contact (with protective shield 56 interposed therebetween, where such a shield is utilized).

Accordingly, the auxiliary screws 54 are preferably backed-off (loosened) one turn, and then the main bolt 32 is tightened to the final tension. Finally, if desired and necessary, the auxiliary screws 54 can be tightened to provide additional strength to the assembly.

Thus, my invention provides an adjustable fixture assembly for positioning and aligning prosthetic devices with respect to a wearer's socket, which may be readily and precisely adjusted without the necessity of removing the socket from the wearer. As indicated above, this provides a substantial and valuable improvement over known socket adaptors.

The fixture assembly of my invention has been described with some particularity but the specific designs and constructions disclosed are not to be taken as delimiting of the invention in that various modifications will at once make themselves apparent to those of ordinary skill in the art, all of which will not depart from the essence of the invention and all such changes and modifications are intended to be encompassed within the appended claims.

I claim:

1. An assembly for adjustably securing a prosthesis to a socket operatively secured to an amputee's stump, wherein the prosthesis is adjustable with respect to said socket, comprising:

an upper attachment member for operatively securing to the socket of said amputee, said upper attachment member having a first central opening therethrough;

an intermediate attachment member having a second central opening therethrough, said intermediate attachment member having a partially spherical portion projecting downward from the lower side of said intermediate attachment member about the axis of said second central opening;

a lower attachment member positioned adjacent said intermediate attachment member such that said intermediate attachment member is located between said upper attachment member and said lower attachment member, said lower attachment member having an upper surface with a partially spherical indentation formed therein which receives said partially spherical portion of said intermediate attachment member such that said lower attachment member is in a pivotal relationship with said intermediate attachment member, said lower attachment member also having a third central opening therethrough;

a central bolt extending through said first, second and third central openings, said first central opening being substantially larger than the cross section of said second central opening to permit said upper attachment member to be moved in a lateral manner relative to said intermediate attachment member, wherein said central bolt cooperates with a threaded nut member positioned above said first central opening, wherein said central bolt can be tightened and placed into tension to hold said upper, intermediate and lower attachment members together, said central bolt being utilized to secure said upper attachment member in a predetermined lateral position relative to said intermediate attachment member, and to bring said partially spherical portion into engagement with said partially spherical indentation such that said partially spherical portion substantially nests within said partially spherical indentation, wherein at least a portion of a vertical compression load imposed on said assembly by said amputee during utilization of said prosthesis is borne directly by said engagement of said partially spherical portion and said partially spherical indentation, wherein said central bolt can be used to provide a coarse, angular adjustment of said lower attachment member relative to said intermediate attachment member, said central bolt having a head extending downwardly from said third central opening, wherein said lower attachment member has a clamp to permit said prosthesis to be removed, wherein said central bolt can be tightened from underneath said lower attachment member without having to remove said assembly from said socket; and a plurality of threaded bores located on said lower attachment member, and a plurality of threaded bolts associated therewith, said threaded bores being located at a predetermined distance from the center of said lower attachment member such that by adjusting said threaded bolts, the angle of said lower attachment member can be adjustably determined more precisely than by said central bolt alone, said threaded bolts being aligned at an upwardly oriented angle relative to said lower attachment member such that each of said threaded bolts can directly transmit a portion of said vertical compression load imposed on said assembly by said amputee.

2. The assembly of claim 1, wherein said first central opening of said upper attachment member is a square opening, and said threaded nut member is substantially eye-shaped, the cooperation therebetween enabling maximum lateral adjustability between said upper and intermediate attachment members.

3. The assembly of claim 1, wherein said lower attachment member comprises a partially tubular portion, said partially tubular portion being adapted to fit snugly over a tubular portion of said prosthesis.

4. The assembly of claim 3, wherein said partially tubular portion has a tube clamp, wherein by adjusting said tube clamp, said tubular portion of said prosthesis can be adjustably secured to said assembly.

5. The assembly of claim 1, further comprising a washer positioned on the upper side of said upper attachment member, said washer comprising a central opening through which said central bolt may extend, said threaded nut washer having a concave, partially spherical indentation about the axis of said central opening, wherein a convex, partially spherical member mates with said concave, partially spherical indentation of said washer, said convex member having an opening through which said central bolt extends, the relative movement between said convex member and said concave member permitting said central bolt to pivot about said washer.

6. The assembly of claim 5, wherein said second and third central openings are aligned together such that they form a frustoconical internal shape which permits said central bolt to be positioned at a slight angle relative to said upper attachment member.

7. The assembly of claim 1, wherein said lower attachment member has a partially spherical downwardly projecting surface adjacent said third central opening, said downwardly extending head of said central bolt having a concave partially spherical member which receives said partially spherical downwardly projecting surface adjacent said third central opening, the interrelationship therebetween permitting said lower attachment member to move angularly relative to said central bolt.

8. The assembly of claim 1, wherein a shield is provided on the lower side of said intermediate attachment member, said shield protecting said intermediate attachment member from excessive wear caused by said threaded bolts engaging said intermediate attachment member.

9. The assembly of claim 1, wherein said second and third central openings are aligned together such that they form a substantially frustoconical shape to permit said central bolt to be positioned at a slight angle relative to said upper attachment member.

10. The assembly of claim 1, wherein said third central opening of said lower attachment member is larger than the cross section of said central bolt to permit said lower attachment member to be moved in a translatory manner relative to said central bolt.

11. The assembly of claim 1, wherein a plurality of recesses are provided on the lower side of said intermediate attachment member, each of said recesses receiving one of said threaded bolts.

12. The assembly of claim 1, wherein said second and third central openings are aligned such that said lower attachment member can pivot freely about said partially spherical portion of said intermediate attachment member.

13. An assembly for adjustably securing a prosthesis to a socket operatively secured to an amputee's stump, wherein the prosthesis is adjustable with respect to said socket, comprising:
   an upper attachment member for operatively securing to the socket of said amputee, said upper attachment member having a first central opening therethrough;
   an intermediate attachment member having a second central opening therethrough, said intermediate attachment member having a partially spherical portion projecting downward from the lower side of said intermediate attachment member about the axis of said second central opening;
   a lower attachment member positioned adjacent said intermediate attachment member, such that said intermediate attachment member is located between said upper attachment member and said lower attachment member, said lower attachment member having an upper surface with a partially spherical indentation formed therein which receives said partially spherical portion of said intermediate attachment member such that said lower attachment member is in a pivotal relationship with said intermediate attachment member, said lower attachment member also having a third central opening therethrough;
   a central bolt extending through said first, second and third central openings, said first central opening being substantially larger than the cross section of said central bolt to permit said upper attachment member to be moved in a lateral manner relative to said intermediate attachment member, wherein by tightening said central bolt, said central bolt is placed into tension and holds said upper, intermediate and lower attachment members together, said central bolt being utilized to secure said upper attachment member in a predetermined lateral position relative to said intermediate attachment member, and to provide a coarse angular adjustment of said lower attachment member relative to said intermediate attachment member, said tightening of said central bolt bringing said partially spherical portion into engagement with said partially spherical indentation such that at least a portion of a vertical compression load imposed on said assembly by said amputee is borne directly by said engagement of said partially spherical portion and said partially spherical indentation; and
   a plurality of threaded bores located on said lower attachment member, and a plurality of threaded bolts associated therewith, said threaded bores being located at a predetermined distance from the center of said lower attachment member such that by adjusting said threaded bolts, the angle of said lower attachment member can be adjustably determined more precisely than by said central bolt alone, said threaded bolts being aligned at an upward angle relative to said lower attachment member such that each of said threaded bolts can transmit a portion of the compression load imposed on said assembly by said amputee.

14. The assembly of claim 13, wherein said second and third central openings are aligned together such that they form a substantially frustoconical shape to permit said central bolt to be positioned at a slight angle relative to said upper attachment member.

15. The assembly of claim 13, wherein said third central opening of said lower attachment member is larger than the cross section of said central bolt to permit said lower attachment member to be moved in an angular and translatory manner relative to said central bolt.

16. The assembly of claim 13, wherein said central bolt has a head extending downwardly from said third central opening, wherein said lower attachment member has a clamp to permit said prosthesis to be removed, wherein said central bolt can be tightened from underneath said lower attachment member without having to remove said assembly from said socket.

17. The assembly of claim 13, wherein a plurality of recesses are provided on the lower side of said intermediate attachment member, each of said recesses receiving one of said threaded bolts.

18. The assembly of claim 13, wherein a shield is provided on the lower side of said intermediate attachment member, said shield protecting said intermediate attachment member from excessive wear caused by said threaded bolts engaging said intermediate attachment member.

* * * * *